US009308477B2

(12) United States Patent
Treharne et al.

(10) Patent No.: US 9,308,477 B2
(45) Date of Patent: Apr. 12, 2016

(54) SYRINGELESS FILTER DEVICE COMPRESSOR

(75) Inventors: David Gwyn Treharne, Newport (GB); Stevan Paul Tortorella, Wells, ME (US)

(73) Assignee: GE HEALTHCARE UK LIMITED, LIttle Chalfont (GB)

( * ) Notice: Subject to any disclaimer, the term of this patent is extended or adjusted under 35 U.S.C. 154(b) by 108 days.

(21) Appl. No.: 14/129,586

(22) PCT Filed: Jun. 26, 2012

(86) PCT No.: PCT/EP2012/062331
§ 371 (c)(1),
(2), (4) Date: Dec. 27, 2013

(87) PCT Pub. No.: WO2013/000897
PCT Pub. Date: Jan. 3, 2013

(65) Prior Publication Data
US 2014/0134079 A1    May 15, 2014

(30) Foreign Application Priority Data
Jun. 29, 2011 (GB) .................................. 1111080.6

(51) Int. Cl.
*B01D 35/30* (2006.01)
*B01L 3/02* (2006.01)
(Continued)

(52) U.S. Cl.
CPC ............. *B01D 35/301* (2013.01); *B01L 3/0289* (2013.01); *B01L 3/502* (2013.01);
(Continued)

(58) Field of Classification Search
CPC .......... B01L 2300/0681; B01L 3/0289; B01L 2400/0478; B01L 3/5021; B01L 3/561; B01L 9/00
See application file for complete search history.

(56) References Cited

U.S. PATENT DOCUMENTS 2,591,510 A * 4/1952 Clark ...................... A47J 19/02
100/229 A
2,639,613 A * 5/1953 Richmond ............... G01N 3/00
177/208

(Continued)

FOREIGN PATENT DOCUMENTS

GB          2 392 854          3/2004
WO          WO 98/22212        5/1998

OTHER PUBLICATIONS

Whatman Compressor for Mini-UniPrep 2002, pp. 1-2.*
(Continued)

*Primary Examiner* — Tatyana Zalukaeva
*Assistant Examiner* — Guy K Townsend
(74) *Attorney, Agent, or Firm* — Sutherland Asbill & Brennan LLP

(57) ABSTRACT

Embodiments of the invention relate to a syringeless filter device compressor for compressing one or more syringeless filter devices. Such syringeless filter devices are typically compressed entirely by hand; however, this may be uncomfortable and/or dangerous for the operator. In embodiments of the present invention, there is provided an apparatus comprising a holder for holding a plurality of syringeless filter devices in a two-dimensional array, and a compressor device. The compressor includes a pusher which can be moved by an actuator to compress the filtration devices held in the two-dimensional array. These features enable a compact compressor device for compressing syringeless filter devices, without the operator being in contact with the syringeless filter device during the compression process.

19 Claims, 7 Drawing Sheets

(51) Int. Cl.
    *B01L 3/00*     (2006.01)
    *G01N 1/40*     (2006.01)
    *G01N 35/00*     (2006.01)
    *G01N 35/10*     (2006.01)

(52) U.S. Cl.
    CPC ........... *B01L 3/5021* (2013.01); *G01N 1/4005* (2013.01); *G01N 1/4077* (2013.01); *B01L 2200/025* (2013.01); *B01L 2200/0684* (2013.01); *B01L 2300/0681* (2013.01); *B01L 2400/0478* (2013.01); *G01N 2001/4088* (2013.01); *G01N 2035/00475* (2013.01); *G01N 2035/1053* (2013.01)

(56) References Cited

U.S. PATENT DOCUMENTS

| | | |
|---|---|---|
| 4,424,279 A | 1/1984 | Bohn et al. |
| 4,587,221 A * | 5/1986 | Cais ................... G01N 33/537 210/359 |
| 4,644,807 A | 2/1987 | Mar |
| 4,921,618 A | 5/1990 | Hamlin |
| 5,482,626 A | 1/1996 | Lohnes et al. |
| 6,379,565 B1 * | 4/2002 | Guirguis .............. G01N 1/2813 210/767 |
| 7,816,142 B1 | 10/2010 | Frasca |
| 2008/0146917 A1 | 6/2008 | Freund |
| 2009/0238725 A1 | 9/2009 | Ellis et al. |
| 2010/0224012 A1 | 9/2010 | Modic et al. |
| 2014/0134079 A1 * | 5/2014 | Treharne ............... B01L 3/0289 422/534 |
| 2014/0234125 A1 * | 8/2014 | Treharne ............... B01L 3/0289 417/53 |

OTHER PUBLICATIONS

Whatman, Whatman Compressor for Mini-Uni-Prep, 2001, pp. 1-2, Whatman, Clifton, NJ; www.whatman.com.*

* cited by examiner

SYRINGELESS FILTER DEVICE COMPRESSOR

FIELD OF THE INVENTION

The present invention relates to a syringeless filter device compressor for use in filtering laboratory sample filtration devices holding liquid to be filtered.

BACKGROUND OF THE INVENTION

Filtration devices are frequently employed in laboratory and other environments to remove solids from a liquid sample. Liquid samples, for example, biological samples such as blood and urine, may be filtered to remove particulate matter such as contaminants or unwanted protein. The filtrate may then be used to perform laboratory tests, such as high-performance liquid chromatography (HPLC) analysis.

Some laboratory filtration devices, typically referred to as "syringe filters", include a standard laboratory syringe, into which a liquid sample to be filtered is drawn. A syringe filter is then fitted to the tip of the syringe and the syringe plunger is compressed, forcing the liquid sample contained within through the syringe filter into a separate receptacle. However, use of syringe filters according to the above procedure can be time consuming, and due to the number of components required, can be relatively costly.

Alternative laboratory filtration devices, referred to as "syringeless filters", in which no syringe is used have been developed, such as the Whatman™ Mini-Uniprep™. FIG. 1 shows an exemplary syringeless filter device 100, in assembled form. The device 100 comprises a vial 102 (typically having a capacity of approximately 0.4 ml) for holding a liquid sample 104 to be filtered. The device 100 also comprises a hollow plunger 106 having a filtration membrane 108 at one end, and a pre-attached cap 110 at the other end. During filtration, the device 100 is compressed so that the plunger 106 slides towards the bottom of the vial 102; as the plunger 106 slides, a seal 112 on the exterior walls of the plunger 106 engages with the internal walls of the vial 102, preventing the liquid sample 104 from passing around the outside of the plunger 106. Accordingly, the liquid sample 104 is forced through the filtration membrane 108, and into the interior of the plunger 106 where it collects as a filtrate 114, leaving filtered particles in the bottom of the vial 102. Vents 116 in the body of the plunger 106 allow air to escape as the plunger 106 fills. When the device 100 is fully compressed, a locking ring 118 engages with the inner wall of the vial 102 to form an air-tight seal. The filtrate 114 can then be stored or transported in this state for extended periods (typically up to several days) until it is needed, at which time it may be removed from the plunger by, for example, using a syringe needle to pierce a septa seal 120 in the cap 110.

Whilst the term "syringeless filter device" is used herein, an alternative term often used is "filter vial", as in the case of the Thomson SINGLE StEP™ Filter Vial device; such devices perform the same function as the syringeless filter device described above and may be operated in the same way.

Syringeless filter devices such as those described above are simpler to use than syringe filters, and typically have fewer parts, making them simpler to manufacture than syringe filters.

The step of compressing the syringeless filter device may be performed manually, with a human operator pressing the plunger into the vial using their hand. However, this may be time consuming, and can be uncomfortable for the operator, since the force required to push the plunger into the vial may be significant, due to the sealing contact described above. Further, the compression process can result in breakage of the syringeless filter device, especially where glass components are used, and leakage of the sample. This poses a risk of injury to the operator, as well as potentially bringing him or her into contact with the sample to be filtered; in particular, where the sample is held in a potentially harmful solvent such as acetonitrile or methanol, such contact is undesirable.

The Whatman™ Six Position Compressor™ is a device for compressing multiple syringeless filter devices in a single action. The device comprises a base fixed to a hand lever via a pivot. The base includes six shallow recesses, arranged in a straight line, for locating syringeless filter devices for compression. In use, the hand lever is raised to allow an operator to individually locate each of the uncompressed syringeless filter devices in the recesses. The operator then brings down the hand lever to a horizontal position, and the lever pushes downwards onto each of the syringeless filter devices, and compresses them, in turn.

It is an object of the present invention to provide an improved syringeless filter device compressor.

SUMMARY OF THE INVENTION

In accordance with an aspect of the present invention, there is provided a syringeless filter device compressor for use in filtering laboratory samples comprising liquid to be filtered, the syringeless filter device compressor being adapted for compressing a plurality of syringeless filter devices, each being compressible by movement of a first part of the syringeless filter device towards a second part of the syringeless filter device, the second part of the syringeless filter device being for holding a laboratory sample to be filtered, said movement of the first part of the syringeless filter device resulting in the laboratory sample being filtered to provide filtered liquid, the syringeless filter device compressor comprising:

a support structure;

compression means connected to said support structure and capable of moving with respect thereto from a first position to a second position;

actuation means for actuating the compression means to move from said first position to said second position; and a syringeless filter device holder for holding a plurality of said syringeless filter devices in a plurality of corresponding plurality of predefined positions forming a two-dimensional array, whereby, when one or more syringeless filter devices are held in said syringeless filter device holder such that said first part of a given syringeless filter device is between the first and the second positions, said actuation results in said first part of the given syringeless filter device moving towards said second part of the given syringeless filter device. This provides various advantages. For example, since the syringeless filter device holder positions form a two-dimensional array, a syringeless filter device compressor can be provided in a relatively compact form.

In some embodiments, the syringeless filter device holder comprises a top surface having a plurality of recesses for holding said plurality of syringeless filter devices. Holding the syringeless filter devices in recesses inhibits a liquid sample from passing to the exterior of the holder, in the event of a syringeless filter device leaking.

Preferably, the syringeless filter device holder comprises a plurality of gaps in a side wall, each said gap extending from said side wall to a said recess, whereby at least a part of the interior of said recess is visible through a said gap. These features enable visual inspection of a syringeless filter device held in the holder.

Preferably, the syringeless filter device compressor comprises a transparent seal locatable in a said gap for inhibiting fluid passing from a said recess to the exterior of the syringeless filter device holder. This inhibits leaking whilst allowing visual inspection of a syringeless filter device held in the holder.

The syringeless filter device holder may comprise a groove in said top surface for holding the transparent seal, the groove intersecting with said plurality of gaps. The groove may be substantially circular, with the seal comprising a ring.

Each of the plurality of recesses may be substantially cylindrical.

Preferably, the support structure defines a holder position, and the syringeless filter device holder is removably locatable at said holder position.

These features enable the holder to be loaded with syringeless filter devices prior to being placed at the holder position. It is thus not necessary to provide space within the syringeless filter device compressor to enable the operator to place the syringeless filter devices in the holder, meaning that the syringeless filter device compressor can be compact.

Further, when the syringeless filter device holder is removable, multiple holders can be pre-loaded for compression in quick succession by the same syringeless filter device compressor, improving efficiency of the compression process.

Preferably, the support structure comprises a holder locating portion defining said holder position, the holder locating portion having a surface arrangement corresponding to an external surface of the syringeless filter device holder, whereby said holder is positively locatable in the holder position by slideable movement into the holder position.

Preferably, the syringeless filter device holder has a substantially circular external surface, in cross-section, and the holder locating portion has a part-circular surface arrangement matching said substantially circular external surface.

In some embodiments, the syringeless filter device compressor comprises inhibiting means for inhibiting said compression means from moving past said second position towards said holder position. This prevents the syringeless filter devices from being over-compressed.

In some embodiments, the syringeless filter device holder comprises said inhibiting means, and said inhibiting means is located substantially centrally of said two-dimensional array, ensuring even distribution of pressure applied to the syringeless filter devices. In some embodiments, the inhibiting means comprises a stop pin, and the syringeless filter device holder comprises a recess for holding said stop pin. The length of the stop pin may be chosen according to the size of syringeless filter device being compressed and ensures that potentially damaging over-compression of the syringeless filter devices is prevented.

Preferably, the syringeless filter device holder is arranged, to hold each of said plurality syringeless filter devices such that the direction along which each said first part moves towards said each said second part is substantially parallel to the direction of movement of the compression means from the first position to the second position. This enables efficient transmission of force from the compression means to the syringeless filter devices, and inhibits dislodging of the syringeless filter devices during the compression process.

In some embodiments, the compression means comprises a substantially planar surface facing said holder locating position, the substantially planar surface facing said two-dimensional array and being arranged to contact the plurality of syringeless filter devices substantially simultaneously during operation of the compression means. Preferably, the movement of the compression means from said first position to said second position is along a direction substantially perpendicular to said substantially planar surface.

In some embodiments, the two-dimensional array is substantially circular.

The actuation means may comprise a manually rotatable lever. The lever may be connected to a gear wheel arranged to engage with a gear rack, the gear rack being connected to the compressions means, whereby rotation of the gear rack results in said movement of the compression means.

Alternatively, or additionally, the actuation means may an electromechanical solenoid or a hydraulic actuator.

In accordance with a second embodiment of the present invention, there is provided a syringeless filter device compressor for use in filtering laboratory samples comprising liquid to be filtered, the syringeless filter device compressor having being adapted for compressing a plurality of syringeless filter devices, each being compressible by movement of a first part of the syringeless filter device towards a second part of the syringeless filter device, the second part of the syringeless filter device being for holding a laboratory sample to be filtered, said movement of the first part of the syringeless filter device resulting in the laboratory sample being filtered to provide filtered liquid, the syringeless filter device compressor comprising:

a support structure;

a pusher connected to said support structure and capable of moving with respect thereto from a first position to a second position, said second position being nearer to the holder position than said first position;

an actuator for actuating the pusher to move from said first position to said second position; and a syringeless filter device holder for holding a plurality of said syringeless filter devices in a plurality of corresponding plurality of predefined positions forming a two-dimensional array, whereby, when one or more syringeless filter devices are held in said syringeless filter device holder such that a said first part of a given syringeless filter device is between the first and the second positions, said actuation results in said first part of the given syringeless filter device moving towards said second part of the given syringeless filter device.

A further aspect of the invention provides the use of a syringeless filter device compressor for compressing a syringeless filter device to filter a laboratory sample.

Further features and advantages of the invention will become apparent from the following description of illustrative embodiments of the invention, given by way of example only, which is made with reference to the accompanying drawings.

DETAILED DESCRIPTION OF THE INVENTION

Figure 2:
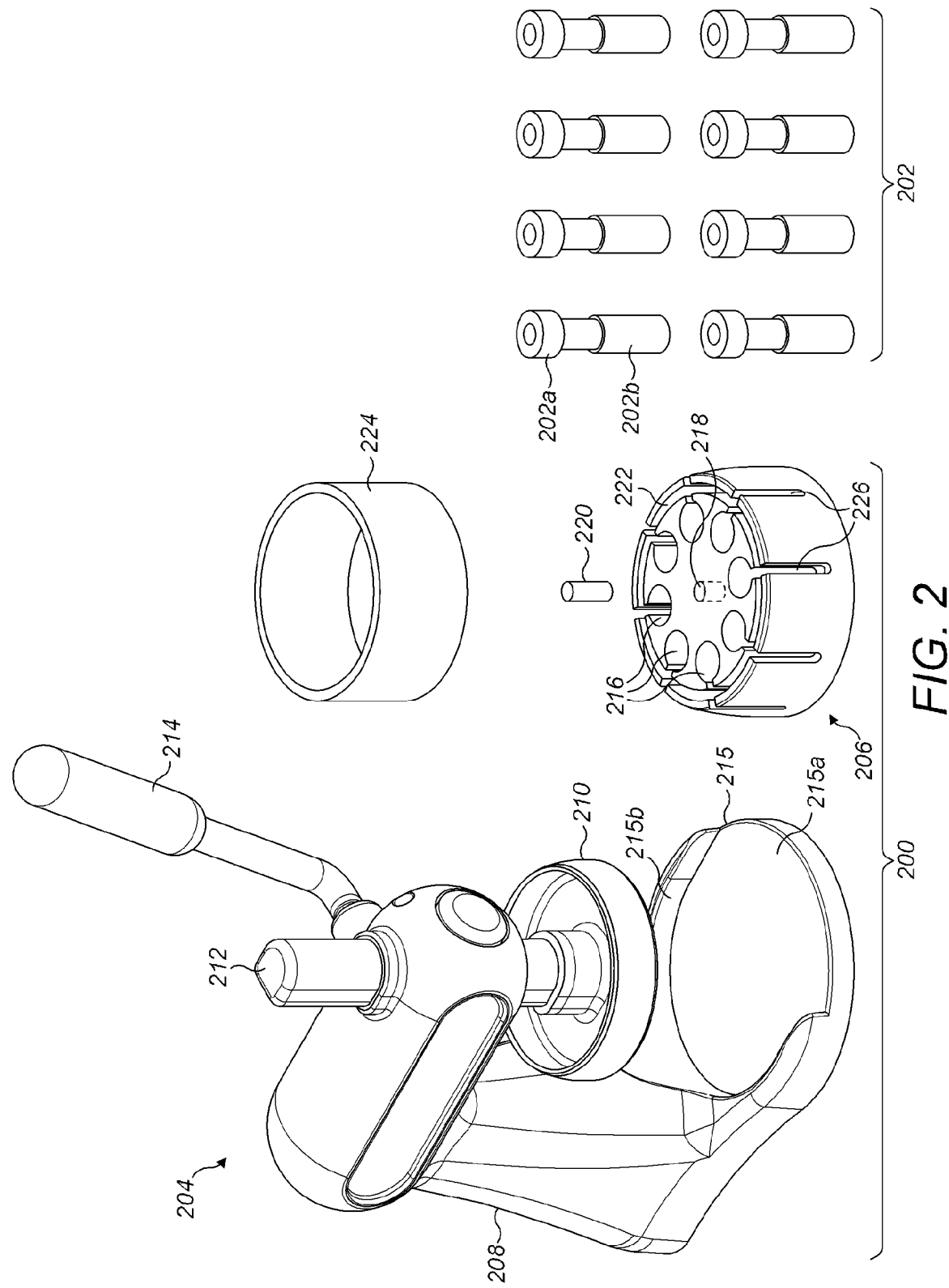
FIG. 2 is a perspective view of a syringeless filter device compressor according to an embodiment of the present invention, and syringeless filter devices for compression by the syringeless filter device compressor.

FIG. 2 shows an exemplary syringeless filter device compressor 200 for compressing laboratory sample syringeless filter devices according to an embodiment of the present invention, along with a set of syringeless filter devices 202 for filtering a laboratory sample. The syringeless filter device compressor 200 includes compression apparatus 204, and a syringeless filter device holder, hereinafter referred to as a "holder" 206.

The compression apparatus 204 includes a support structure, hereinafter referred to as a "compressor body" 208. The compressor body 208 is a rigid structure connected to a compression means, for example a compressor plate 210, via an actuating mechanism held in a casing 212. The actuating mechanism is connected to a manually operable lever 214, which is manually rotatable so as to drive the actuating mechanism, as described below with reference to FIGS. 5a to 5c.

The compressor includes a holder locating portion 215 which defines a holder position at which the holder 206 is located when compressing syringeless filter devices 202 held therein, as described below. The holder locating portion 215 has a flat bottom surface 215a and a curved back surface 215b corresponding respectively to external bottom and side surfaces of the holder 206, so that the latter can be held in place at the holder position. Alternatively, the curved back of the holder locating portion 215 could be replaced by a series of contact points in a part-circular arrangement to define the holder position.

The holder 206 has a top surface which includes recesses, hereinafter referred to as "filter recesses" 216, for holding syringeless filter devices 202 at predefined positions. In the present example, the holder 206 comprises eight filter recesses 216 arranged in a two dimensional array. In the present example, the filter recesses 216 are arranged in a circular array; however, in some embodiments, other types of two dimensional array may be used, such as a square array. Use of a two-dimensional array provides a compact arrangement for holding multiple syringeless filter devices 202, allowing the holder 206, and consequently the compression apparatus 204, to have a compact form.

A series of gaps, in the form of slits 226 extend from each of the filter recesses 216 to a side wall of the holder 206, so that the interior of each of the filter recesses 216 is visible through a corresponding slit 226. This enables visual inspection of a filter device 202 held in a filter recess 216.

The top surface of the holder 206 has a further recess, hereinafter referred to as a stop pin recess 218, for holding a stop pin 220, and a locating groove 222 for holding a ring seal 224, the locating groove intersecting each of the slits 226. These components will be described in more detail below.

The filter recesses 216 are dimensioned appropriately to hold filter devices 202 of predefined dimensions. In the example shown in FIG. 2, the filter devices 202 and filter recesses 216 each have a circular cross-section; the internal diameter of each of the filter recesses 216 may be chosen to be approximately the same as an external diameter of a corresponding filter device 212, so that the latter may be inserted into the former, and held in place by an interference fit.

Figure 3:
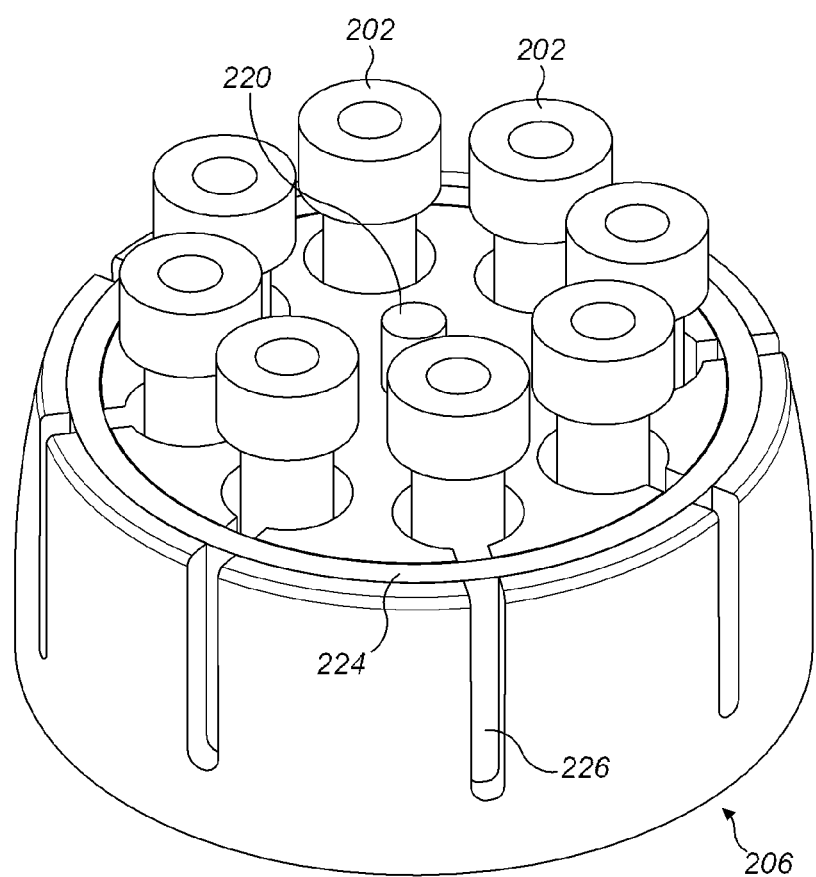
FIG. 3 is a perspective view of a syringeless filter device holder, for use in some embodiments of the present invention holding, uncompressed syringeless filter devices.

The filter recesses 216 may be labelled, for example numbered, as shown in FIG. 3; this facilitates traceability of the samples being filtered.

Figure 1:
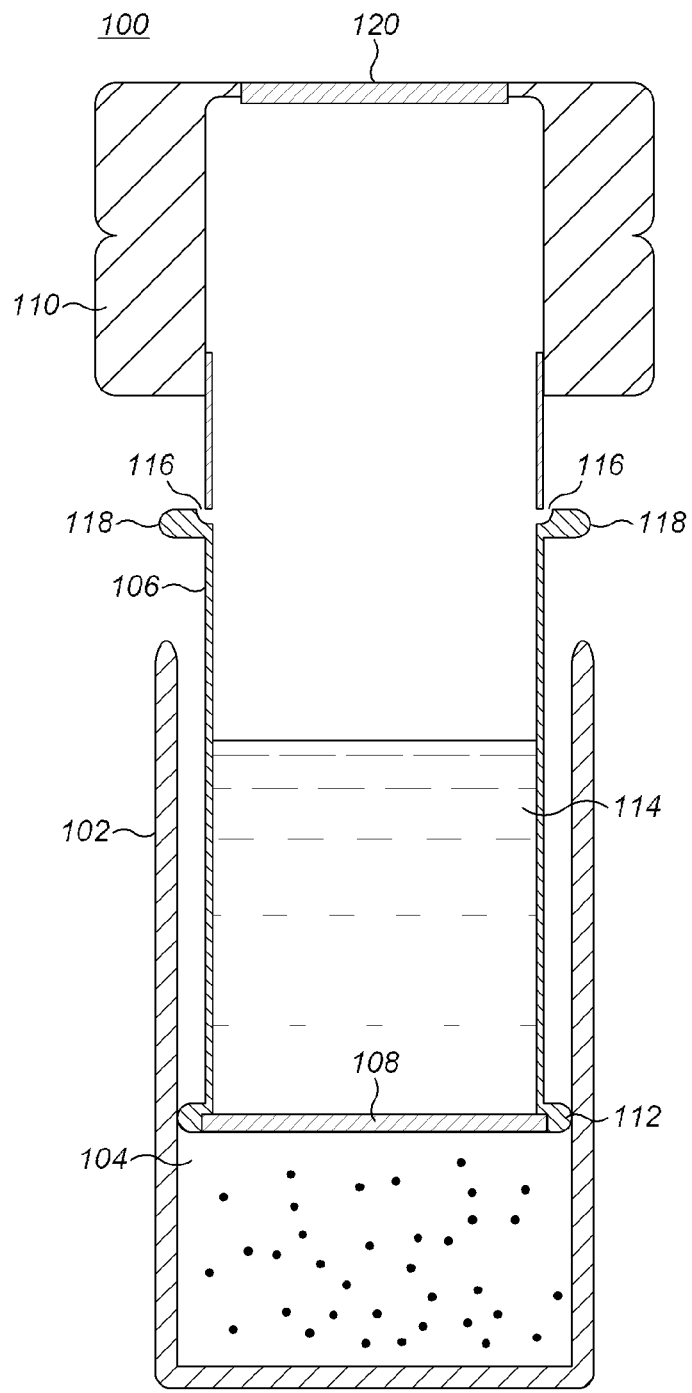
FIG. 1 is a cross-sectional view of an exemplary syringeless filter device for compression using a syringeless filter device compressor according to an embodiment of the present invention.

The syringeless filter devices 202 for compression by syringeless filter device compressor 200 according to embodiments of the present invention have a first part, in the form of a plunger 202a and a second part, in the form of a vial 202b. During filtration, the syringeless filter devices 202 are compressed to filter a laboratory sample initially held in the vial 202b, as described above with reference to FIG. 1.

FIG. 3 shows a holder 206 with the uncompressed syringeless filter devices 202, stop pin 220 and ring seal 224 held in the filter recesses 216, stop pin recess 218 and locating groove 222 respectively. The uncompressed syringeless filter devices 202 each contain a laboratory sample (not shown) to be filtered; the laboratory samples may be inserted into respective vials 202b prior to syringeless filter devices 202 being inserted into the filter recesses 216, or the vials 202b may first be inserted into the filter recesses 206, with the respective laboratory samples then inserted into the vials 202b and the plungers 202a subsequently placed in the respective vials 202b for compression. In the latter case, the slits 226 may be used to view the vial as the sample is inserted, so as to ensure that the vials 212 are filled to an appropriate level.

The seal ring 224 forms a liquid seal with the locating groove 222, so that, if a syringeless filter device 202 breaks, or otherwise leaks, whilst held in the holder 206, the laboratory sample, and associated liquids, are inhibited or prevented from passing through the gaps, so that any leaked liquid sample is held in a filter recess 216, without passing to the exterior of the device. The seal ring 224 is preferably transparent, so that the interior of the filter recesses 216 remains visible via the slits 226.

The seal ring 224 may be held in the locating groove 222 by an interference fit. The seal ring 224 may be removable; this facilitates cleaning of the seal ring 224 and the holder 206, in the event of a sample leakage, for example. However, in some embodiments of the present invention, the seal ring 224 is permanently fixed in the locating groove, using an adhesive, for example.

In the present example, a seal ring 224 is used. However, in some embodiments, other types of seal may be used; for example, there may be a separate linear locating groove intersecting each slit 226 associated with a respective filter recess 216, with individual planar seals locatable in the individual locating grooves.

Figure 4:
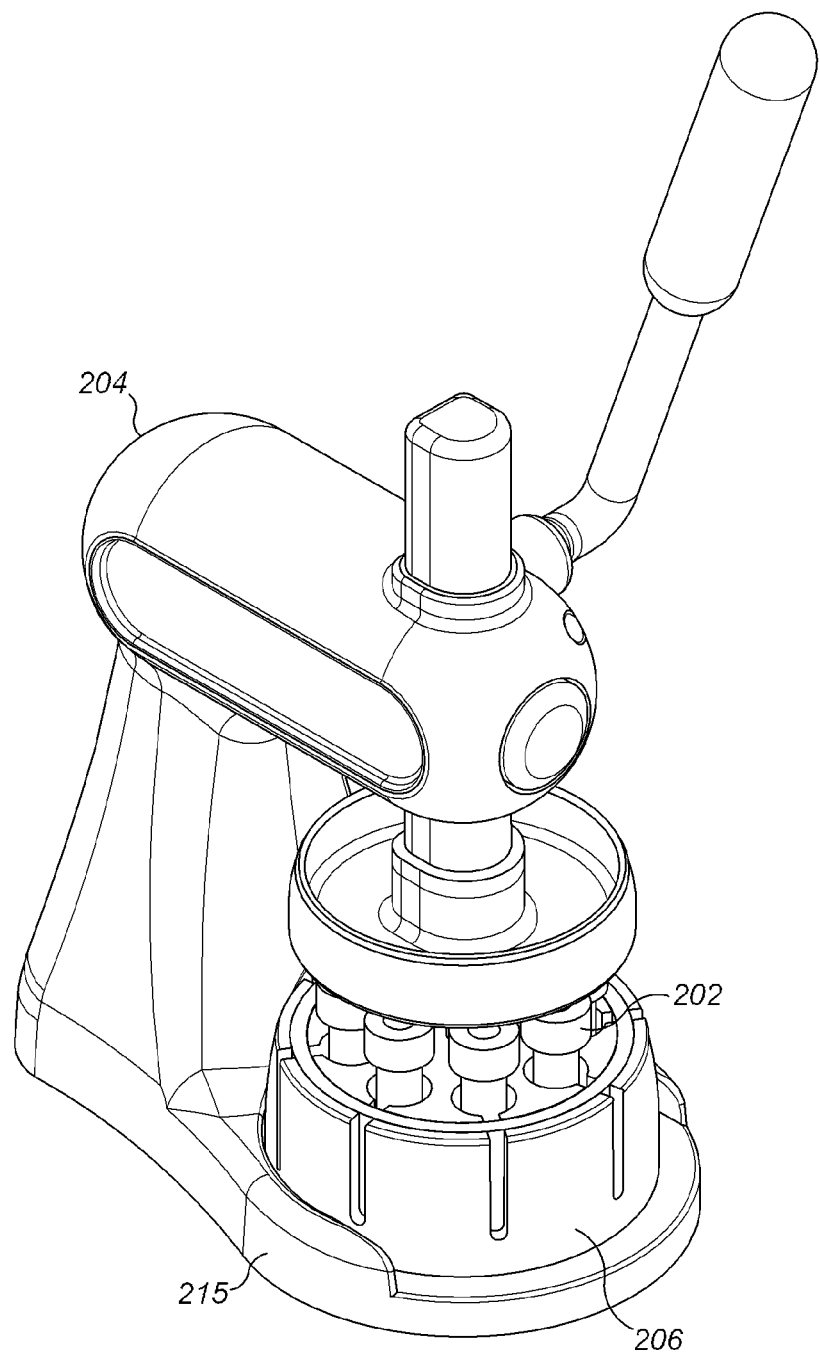
FIG. 4 is a perspective view of syringeless filter device holder of FIG. 2 located in a syringeless filter device compressor according to an embodiment of the present invention.

The holder 206 containing the uncompressed filter devices 202 is placed in the holder locating portion 215 of the compression apparatus 204, as shown in FIG. 4. As mentioned above, the shape and size of the surfaces of the holder locating portion 215 are arranged to substantially match corresponding exterior surfaces of the holder 206, so as to provide a flush fit between the holder 206 and the holder locating portion 215, so that the holder 206 is held in place at a holder position suitable for compressing the syringeless filter devices 202 held therein.

In the present example, the holder 206 has a circular cross-section; this enables the holder 206 to be compact and easy to handle. In particular, the circular holder 206 is easy to insert into the holder locating portion 215, since, provided it is held horizontally, or approximately so, the holder 206 can be slid into the holder locating portion using any orientation. Furthermore, a circular cross-section allows easy viewing of syringeless filter devices 102 held in the holder 206 via the slits 226. However, in some embodiments of the invention, the holder 206 has a non-circular cross-section, such as a square cross-section.

The operation of the syringeless filter device compressor 200 in compressing syringeless filter devices is now described with reference to FIGS. 5a, 5b, and 5c, which show cross-sectional views of the compression apparatus 204 and the holder 206, the latter being located in the holder locating portion 215 and holding syringeless filter devices 202.

The lever 214 is connected to an actuating mechanism comprising a gear wheel 230 and a gear rack 232, the latter being connected to the compression plate 210. Rotation of the lever 214 causes rotation of the gear wheel 230; the teeth of the gear wheel 230 engage with corresponding teeth on the gear rack 232, thereby causing the rack, and consequently the compression plate 210 to move vertically towards or away from the holder 206.

Figure 5A:
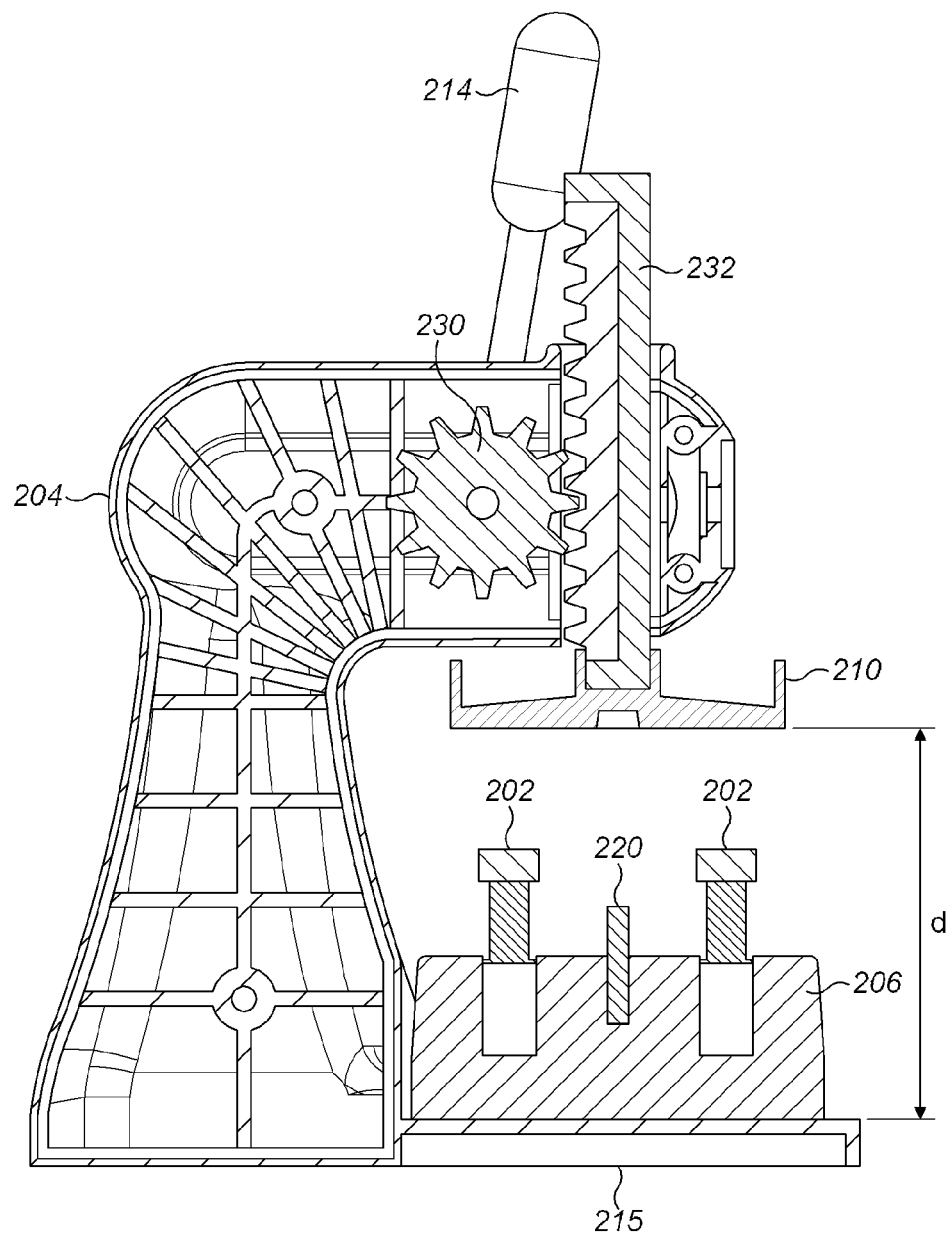
FIGS. 5a, 5b and 5c are cross-sectional views of a syringeless filter device compressor being used to compress syringeless filter devices, in accordance with an embodiment of the present invention.

As shown in FIG. 5a, the compression plate 210 is initially held at a raised position, away from the holder position, so that the holder 206 containing uncompressed filter devices can be inserted into the holder locating portion 215. Since, in the present example, the holder 206 is removable, the uncompressed syringeless filter devices 202 can be inserted into the holder 206 prior to the latter being located in the holder locating portion 215. It is therefore not necessary to provide space for an operator to insert the syringeless filter devices 202 into the holder 206 while the latter is in located in the holder locating portion 215; accordingly, the distance d between the holder locating portion 215 and the compressor plate 215 when the latter is at its maximally raised position, as shown in FIG. 5a, can be small, enabling the compression apparatus 204 to be compact.

Figure 5B:
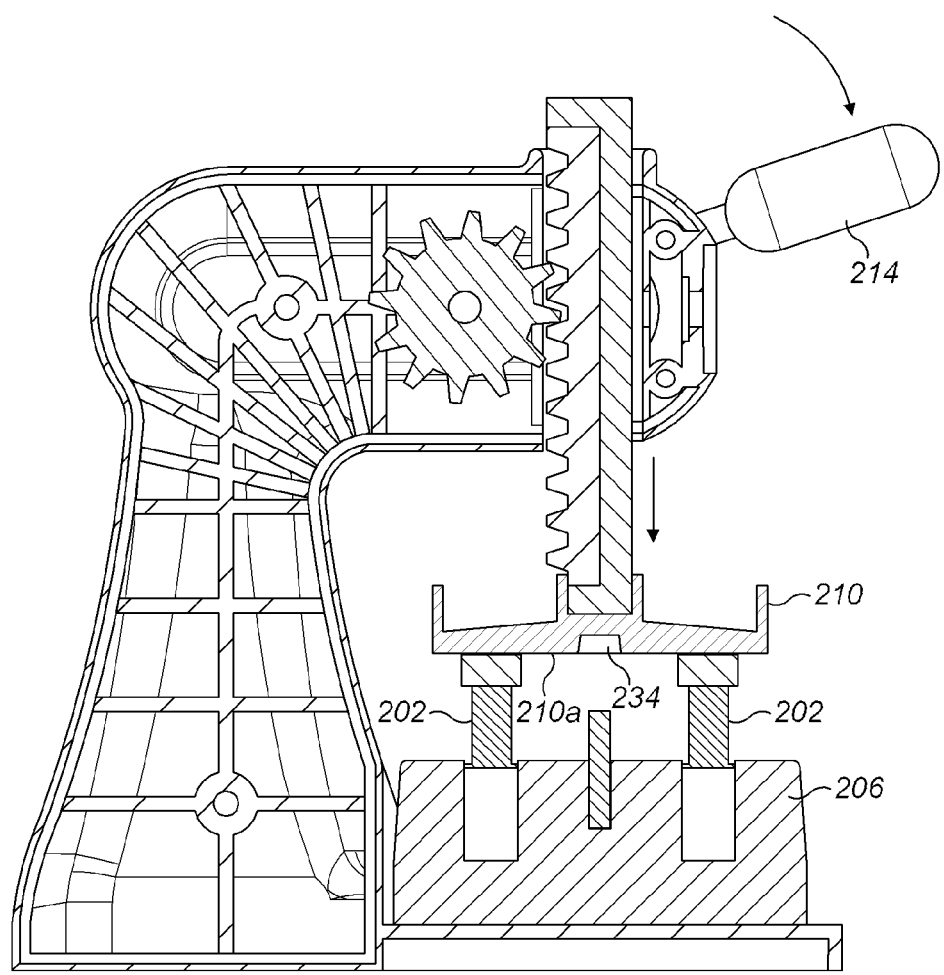

As the lever 214 is rotated downwards, the lower surface 210a of the compressor plate 210 facing the holder 206 is brought into contact with the uncompressed syringeless filter devices 202 held in the holder 206, as shown in FIG. 5b. Further downward movement of the lever 214 results in the compressor plate 210 moving further downwards, thereby compressing the filter devices 202 held in the holder 206. The downward movement of the compressor plate 220 is limited by the stop pin 220, which stops the compressor plate 220 at a position at which the syringeless filter devices 202 are fully compressed; the stop pin 220 thus prevents the compressor plate 220 from moving past the position at which the syringeless filter devices 202 are fully compressed, thereby inhibiting over-compression, and consequential breakage, of the syringeless filter devices 202.

Figure 5C:
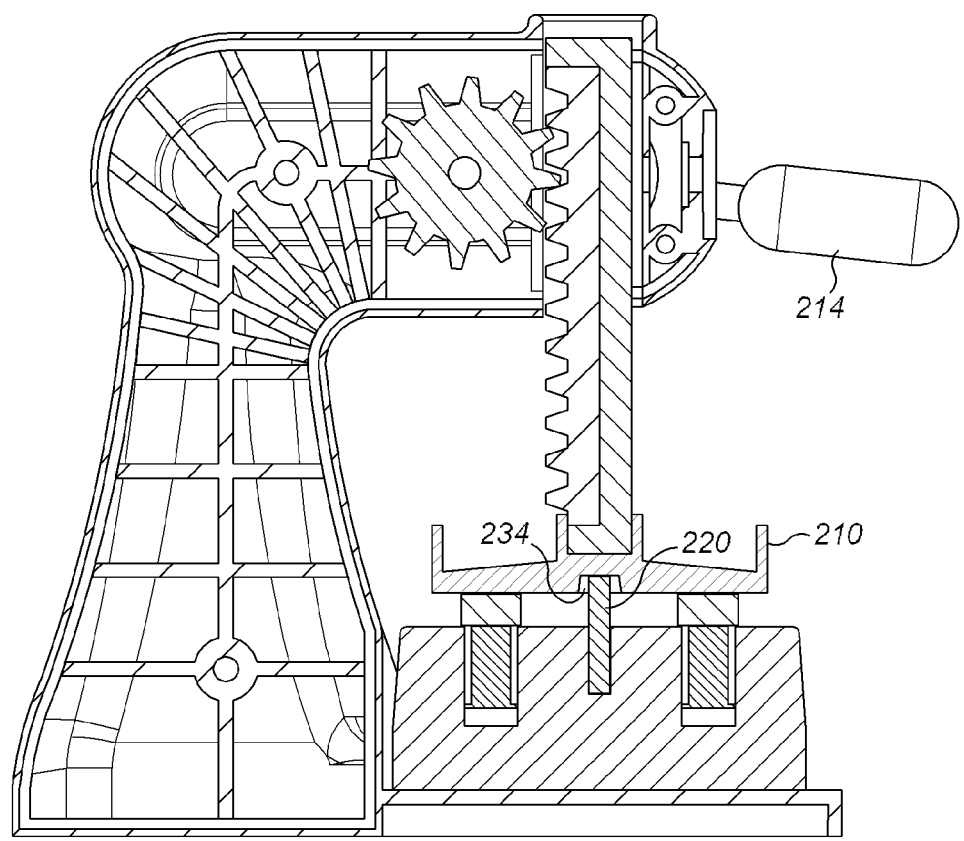

The movement of the compressor plate 210 between the raised position shown in FIG. 5a, and the lowered position shown in FIG. 5c is linear along a vertical line. Further, the holder 206 is arranged to hold the filter devices 202 such that the direction of compression (i.e. the direction along which the plunger 202a moves towards the vial 202b) is also vertical. Accordingly, since the direction of compression is thus parallel to the direction of movement of the compressor plate 210, and since the lower surface 210a of the compressor plate is substantially perpendicular to the direction of compression, the pushing force exerted on the syringeless filter devices 202 by the compressor plate 210 is substantially along the direction of compression, minimising the effort required on the part of the operator rotating the lever, and reducing the risk of a filter device 202 becoming dislodged during the compression process.

Since the movement of compressor plate 210 is linear, the force applied to each syringeless filter device during compression is substantially the same for each syringeless filter device 202. Further, since the array of positions in which the syringeless filter devices 202 are held forms a surface corresponding in shape to the lower surface 210a of the compression plate 210 (in the present example, both surfaces being horizontal and planar), as the compressor plate 210 is lowered, it engages with each of the syringeless filter devices 202 substantially simultaneously. The magnitude of the force applied, and the length of the compression stroke, are thus substantially uniform across the array of filter devices 202.

The compressor plate 210 preferably includes a stop pin indent 234 for locating the stop pin 220; this inhibits the stop pin 220 from slipping on the lower surface 210a of the compressor plate 210, thereby facilitating a smooth compression process. Further, although not shown in the Figures, in some embodiments, the lower surface 210a of the compressor plate includes one or more indents for locating one or more syringeless filter devices 202.

The stop pin 220 is held substantially in the centre of the two-dimensional array of filter recesses 216; this inhibits the downward force on the compressor plate 210 from causing the compressor plate 110 to lean away from a horizontal orientation, causing one or more of the syringeless filtration devices 202 from being over-compressed.

The stop pin 220 may be held in the stop pin recess 218 by an interference fit. The stop pin 220 may be removable; it may then be replaced with a stop pin having a different length, so as to adjust the maximum downward movement of the compressor plate 210, so that syringeless filter devices 202 having different compression requirements can be used, for example. However, in some embodiments, the stop pin 220 is permanently fixed in the stop pin recess 218, using an adhesive, for example. In some other embodiments, no stop pin 220 is used; in these other embodiments, the downward movement of the compressor plate 210 may instead be limited by, for example, a stop mechanism in the actuating mechanism.

Use of syringeless filter device compressor 200 for compressing multiple syringeless filter devices 202 in accordance with embodiments of the present invention thus enable the syringeless filter devices 202 to be compressed without the user being required to directly be in contact with the syringeless filter devices 202 during the compression process. Since the syringeless filter devices 202 are held in a two-dimensional array, the syringeless filter device compressor 200 can have a compact form, improving ease of use and storage.

The compression apparatus 204 and the holder 206 may each be assembled from injection moulded parts made from a plastics material, such as Acrylonitrile Butadiene Styrene (ABS). The ring seal 224 may be injection moulded from a plastics material such as a polycarbonate material. The stop pin 220 may be made from a plastics or metallic material.

The dimensions of the syringless filtration device compressor 200 are typically selected dependent on the syringeless filtration device 202 with which the syringeless filter device compressor 200 is to be used. In the case of Whatman™ Mini-Uniprep™ syringeless filters, the distance d (see FIG. 5a) between the holder locating portion 215 and the compressor plate 215 when the latter is at its maximally raised position is typically 10 to 20 cm; the internal diameter of a filter recess 216 is approximately 12 mm; the diameter of the holder 206 is approximately 85 mm; and the height of the holder is approximately 35 mm.

The above embodiments are to be understood as illustrative examples of the invention. Further embodiments of the invention are envisaged.

For example, in the above examples, the holder 206 is removably locatable in the compression apparatus 204. As described above, this enables the compression apparatus 204 to be compact. Furthermore, in embodiments in which the holder 206 is removable, it is possible to compress multiple batches of syringeless filter devices 202 in quick succession; multiple holders 206 can be pre-loaded with syringeless filter devices 202, and the pre-loaded holders 202 successively fed into the compression apparatus 204 to compress the pre-loaded syringeless filter devices 202. This enables efficient processing of multiple batches of syringeless filter devices 202.

However, it will be understood that the invention is not limited to embodiments in which the holder 206 is removably locatable in the compression apparatus 204. In some embodiments, the holder 206 may be fixed to the compression apparatus 204, for example using screws.

Further, in the above examples, the holder 206 was held in a holder locating portion 215. However, in some embodiments of the present invention, no such portion is used; instead, the holder 206 may be placed on directly a desk or other surface on which the compression apparatus 204 is placed. In this case, the holder position may be defined simply by the path that the compressor plate 204 follows during compression.

In the above examples, a lever 214 was used in conjunction with a wheel gear 230 and a rack gear 232 to actuate the compressor plate. However, other actuators may be used. For example, in some cases an electromechanical solenoid actuator, or a hydraulic actuator may be used, in which case the actuator may be operated automatically, rather than manually.

Similarly, although a compressor plate 210 having a planar surface was used as the "pusher" for pushing (i.e. compressing) the syringeless filter devices 202, other types of pushers may be used, for example plates having non-planar surfaces.

Although in the above examples the syringeless filter devices 202 were held at predefined positions by filter recesses 216, other means of holding the syringeless filter devices 202, such as clips, may be used.

It is to be understood that although the above examples are described with reference a syringeless filter device in which the filtrate is collected internally, syringeless filtration devices in which the filtrate is collected externally may be used with some embodiments of present invention. For example, syringeless filter devices such as the Whatman™ Autovial™ may be used. The Whatman™ Autovial™ comprises a plunger and a barrel, with the liquid sample to be filtered being initially held in the barrel. The barrel has an opening at one end through which liquid may pass via a filter membrane; during filtering, the plunger is pushed towards the filter membrane, forcing the liquid sample through the filter membrane and through the opening; the filtrate exiting the device is collected in an autosampler vial or any other appropriate container. In embodiments in which externally-collecting syringeless filtration devices are used, the containers for collecting the filtrate could be located in the holder 206, so that a syringeless filter device engages with each of the containers.

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A syringeless filter device compressor comprising:
a support structure;
a compression means connected to said support structure and capable of moving with respect thereto from a first position to a second position;
an actuation means for actuating said compression means to move from said first position to said second position;
a syringeless filter device holder configured to hold a plurality of syringeless filter devices in a corresponding plurality of predefined positions forming a two-dimensional array, wherein said syringeless filter device holder comprises a plurality of gaps in a side wall and a top surface having a plurality of recesses capable of holding said plurality of syringeless filter devices, each said gap extending from said side wall to a said recess, whereby at least a part of an interior surface of said plurality of recesses is visible through said plurality of gaps; and
a transparent seal locatable in said plurality of gaps, wherein said transparent seal is configured to inhibit fluid passing from said plurality of recesses to an exterior surface of said syringeless filter device holder,
wherein, when one or more syringeless filter devices are held in said syringeless filter device holder, actuation of said actuation means results in a first part of said one or more syringeless filter devices moving towards a corresponding second part of said one or more syringeless filter devices.

2. The syringeless filter device compressor of claim 1, wherein said syringeless filter device holder comprises a groove in said top surface, wherein said groove is configured to hold the transparent seal and intersects with said plurality of gaps.

3. The syringeless filter device compressor of claim 2, wherein the groove is substantially circular, and the seal is ring shaped.

4. The syringeless filter device compressor of claim 1, wherein each of said plurality of recesses is substantially cylindrical.

5. The syringeless filter device compressor of claim 1, wherein the support structure defines a holder position, and the syringeless filter device holder is removably locatable at said holder position.

6. The syringeless filter device compressor of claim 5, wherein the support structure comprises a holder locating portion defining said holder position, the holder locating portion having a surface arrangement corresponding to an external surface of the syringeless filter device holder, whereby said syringeless filter device holder is positively locatable in the holder position by slideable movement into the holder position.

7. The syringeless filter device compressor of claim 6, wherein the syringeless filter device holder has a substantially circular external surface, in cross-section, and the holder locating portion has a part-circular surface arrangement matching said substantially circular external surface.

8. The syringeless filter device compressor of claim 1, further comprising an inhibiting means for inhibiting said compression means from moving past said second position towards said syringeless filter device holder.

9. The syringeless filter device compressor of claim 8, wherein said syringeless filter device holder comprises said inhibiting means, and said inhibiting means is located substantially centrally of said two-dimensional array.

10. The syringeless filter device compressor of claim 8, wherein said inhibiting means comprises a stop pin, and said syringeless filter device holder comprises a recess for holding said stop pin.

11. The syringeless filter device compressor of claim 1, wherein the syringeless filter device holder is arranged to hold said plurality of syringeless filter devices such that each said first part moves towards each said second part in a direction substantially parallel to the direction of movement of the compression means from the first position to the second position.

12. The syringeless filter device compressor of claim 1, wherein the compression means comprises a substantially planar surface, the substantially planar surface facing said two-dimensional array and being arranged to contact the plurality of syringeless filter devices substantially simultaneously during operation of the compression means.

13. The syringeless filter device compressor of claim 12, wherein the compression means moves from said first position to said second position along a direction substantially perpendicular to said substantially planar surface.

14. The syringeless filter device compressor of claim 1, wherein the two-dimensional array is substantially circular.

15. The syringeless filter device compressor of claim 1, wherein the actuation means comprises a manually rotatable lever.

16. The syringeless filter device compressor of claim 15, wherein the lever is connected to a gear wheel arranged to engage with a gear rack, the gear rack being connected to the compressions means, whereby rotation of the gear rack results in movement of the compression means.

17. The syringeless filter device compressor of claim 1, wherein the actuation means comprises an electromechanical solenoid.

18. The syringeless filter device compressor of claim 1, wherein the actuation means comprises a hydraulic actuator.

19. A syringeless filter device compressor comprising:
a support structure;
a pusher connected to said support structure and capable of moving with respect thereto from a first position to a second position;
an actuator for actuating the pusher to move from said first position to said second position;
a syringeless filter device holder configured to hold a plurality of syringeless filter devices in a corresponding plurality of predefined positions forming a two-dimensional array, wherein said syringeless filter device holder comprises a plurality of gaps in a side wall and a top surface having a plurality of recesses capable of holding said plurality of syringeless filter devices, each said gap extending from said side wall to a said recess, whereby at least a part of an interior surface of said plurality of recesses is visible through said plurality of gaps; and
a transparent seal locatable in said plurality of gaps, wherein said transparent seal is configured to inhibit fluid passing from said plurality of recesses to an exterior surface of said syringeless filter device holder,
wherein, when one or more syringeless filter devices are held in said syringeless filter device holder, actuation of said actuator results in a first part of said one or more syringeless filter devices moving towards a corresponding second part of said one or more syringeless filter devices.

* * * * *